United States Patent
Postel et al.

(10) Patent No.: US 10,383,985 B2
(45) Date of Patent: Aug. 20, 2019

(54) METHODS AND APPARATUS FOR CHARGING AND EVACUATING A DIFFUSION DRESSING

(75) Inventors: Olivier B. Postel, Redwood City, CA (US); Amie B. Franklin, Mill Valley, CA (US)

(73) Assignee: Oxyband Technologies, Inc., Woodbury, MN (US)

( * ) Notice: Subject to any disclaimer, the term of this patent is extended or adjusted under 35 U.S.C. 154(b) by 1346 days.

(21) Appl. No.: 12/245,869

(22) Filed: Oct. 6, 2008

(65) Prior Publication Data

US 2010/0063462 A1 Mar. 11, 2010

Related U.S. Application Data (60) Provisional application No. 61/095,558, filed on Sep. 9, 2008.

(51) Int. Cl.
| | | |
|---|---|---|
| *A61M 1/00* | (2006.01) | |
| *A61M 35/00* | (2006.01) | |
| A61M 27/00 | (2006.01) | |
| A61M 13/00 | (2006.01) | |
| A61F 13/00 | (2006.01) | |
| A61B 17/50 | (2006.01) | |

(52) U.S. Cl.
CPC .......... *A61M 1/0084* (2013.01); *A61M 35/00* (2013.01); *A61M 2205/8225* (2013.01)

(58) Field of Classification Search
CPC ........ A61M 1/00; A61M 13/02; A61M 27/00; A61F 13/00; A61B 17/50
USPC ................. 604/289, 290, 296, 300
See application file for complete search history.

(56) References Cited

U.S. PATENT DOCUMENTS

| | | | |
|---|---|---|---|
| 3,874,387 A | | 4/1975 | Barbieri |
| 5,370,613 A | * | 12/1994 | Helmy ...................... 604/288.02 |
| 5,636,643 A | * | 6/1997 | Argenta et al. ............... 128/897 |
| 5,865,722 A | | 2/1999 | Heng |
| 6,755,807 B2 | * | 6/2004 | Risk et al. ..................... 604/319 |
| 7,883,494 B2 | * | 2/2011 | Martin .......................... 604/289 |
| 2002/0150720 A1 | | 10/2002 | Howard et al. |
| 2004/0199130 A1 | | 10/2004 | Chornenky et al. |
| 2005/0100937 A1 | | 5/2005 | Holmes |
| 2006/0094995 A1 | * | 5/2006 | Bauer ................... A61F 13/122 602/1 |

(Continued)

FOREIGN PATENT DOCUMENTS

| | | |
|---|---|---|
| WO | 20050046761 A1 | 5/2005 |
| WO | 20060089108 A2 | 8/2006 |

(Continued)

OTHER PUBLICATIONS

Princeton University, Farlex Inc., 2003.*

*Primary Examiner* — Tatyana Zalukaeva
*Assistant Examiner* — Ilya Y Treyger
(74) *Attorney, Agent, or Firm* — Donald R. Boys; Central Coast Patent Agency LLC (57) ABSTRACT

A system for introducing a therapeutic agent into a diffusion device and for enabling evacuation of contents contained therein the diffusion device characterized as having at least one interior reservoir accessible through a penetrable external device layer comprising one or more ports installed or installable to the external device layer, and an agent delivery mechanism coupled to at least one of the ports.

7 Claims, 8 Drawing Sheets

(56) References Cited

U.S. PATENT DOCUMENTS

| | | |
|---|---|---|
| 2006/0100586 A1 | 5/2006 | Karpowicz et al. |
| 2007/0118070 A1 | 5/2007 | Cormier et al. |
| 2008/0125634 A1 | 5/2008 | Ryan et al. |

FOREIGN PATENT DOCUMENTS

| | | |
|---|---|---|
| WO | 20070030601 A2 | 3/2007 |
| WO | 20080036131 A2 | 3/2008 |
| WO | 20090035992 A1 | 3/2009 |

* cited by examiner

METHODS AND APPARATUS FOR CHARGING AND EVACUATING A DIFFUSION DRESSING

CROSS-REFERENCE TO RELATED APPLICATIONS

The present application claims priority to U.S. provisional patent application Ser. No. 61/095,558 filed on Sep. 9, 2008, entitled "METHOD FOR CHARGING AND DISCHARGING A DIFFUSION DEVICE", which is included herein in its entirety at least by reference.

BACKGROUND OF THE INVENTION

1. Field of the Invention

The present invention is in the field medical technologies and more particularly the treatment of tissue via a diffusion type device or dressings, the invention pertaining to charging and evacuation of such devices before use and during use.

2. Discussion of the State of the Art

In the medical field it is often required to treat tissue of patients in a manner which requires an extended period of bandaging or covering with medication diffusing patches or like devices that work to keep tissue moist, promote healing, to prevent maceration, possible infection, or to prevent any jolting or other physical disruption of a particular tissue area.

One example of such a therapeutic device is a multilayered diffusion dressing or device typically applied over a wound or graft to promote new skin growth in an area where the original skin was lost or removed by surgery. Such devices have different names in the art but may be technically referred to as therapeutic diffusion devices because of an active delivery (diffusion) of some therapeutic agent, often delivered in the form of a gas through an interfacing diffusion layer of the dressing or device to the affected tissue over time.

The inventor is aware of a diffusion device for treating tissue packaged according to a unique method the device including more than one device layer and at least one reservoir containing a therapeutic agent. The device is placed over top of a first packaging layer and a second packaging layer is placed over the top of the device. Seals are forged between the second packaging layer and the uppermost layer of the diffusion device and between the first packaging layer and an intermediate device layer. The packaging then may be removed by layer when the device is to be applied to tissue to be treated. Variances to the packaging method just described are also known to the inventor the variances including process variances and packaging material property variances that depend in part on device architecture and the therapeutic nature of the device.

A diffusion device for treating tissue is typically charged with some therapeutic agent that is expelled from the device through a diffusion process one effect there being that the dressing eventually becomes depleted of agent and is no longer therapeutic to the tissue being treated. Most such diffusion devices employ gasses infused into a reservoir in the device, the gases being diffused into a tissue area through a special diffusion layer of the device. Diffusion layers and adhesive layers for application of the dressing over a wound are typically a part of such apparatus.

It would be desirable to be able to charge a diffusion dressing with therapeutic agent both at pre-application and during active treatment of a patients wound or tissue area requiring treatment. Likewise, it would be desirable to be able to evacuate a therapeutic agent or in some cases exudates emanating from treated tissue from the diffusion device while it is being used.

Therefore, what are clearly needed are better methods and apparatus for charging and evacuating a diffusion device. Such methods would enable improved diagnostic and prognostic capabilities and would enable multiple therapies to be applied to a tissue area or wound without requiring removal and replacement of the diffusion device in use on the tissue or wound being treated.

SUMMARY OF THE INVENTION

The problem stated above is it is desirable to be able to charge a diffusion dressing with therapeutic agent both at pre-application and during active treatment of a patients wound or tissue area requiring treatment. But many of the conventional means for charging and evacuating a diffusion device are inefficient and not applicable during use of the device. The inventors therefore considered functional elements of a diffusion device and therapeutic agent delivery systems, looking for elements that exhibit modularity that could potentially be harnessed to provide dynamic charging capability but in a manner that would not create any inconvenience for a patient wearing a diffusion device.

Every therapeutic diffusion device diffuses therapeutic agent into a tissue area to be treated, one by-product of which is an exodus of gases or other agents expelled from the device under pressure. Most such diffusion devices employ an internal reservoir the therapeutic gases or agents are contained in and reservoirs and diffusive layers are typically a part of such apparatus.

The present inventor realized in an inventive moment that if, at the point of use, therapeutic agents including gasses could be caused to charge a diffusion device while the device is in use on a patient, significant convenience and better recovery prognosis might result. The inventor therefore constructed a unique system for evacuating and charging a diffusion device that allowed therapeutic agents including gasses to be infused into the device and evacuated from the device while the devise is in use on a patient. A significant efficiency results with no impediment to convenience of use created.

Accordingly, in one embodiment of the invention, a system for introducing a therapeutic agent into a diffusion device and for enabling evacuation of contents contained therein is provided the diffusion device characterized as having at least one interior reservoir accessible through a penetrable external device layer. The system comprises one or more ports installed or installable to the external device layer, and an agent delivery component operable through at least one of the ports.

In one embodiment the therapeutic agent is one of a gas, a gel, a liquid, an emulsion, a drug, a growth factor, an analgesic, an antibiotic, or an antimicrobial. In one embodiment the one or more ports are pre-installed during manufacture of the diffusion device. In a variation of this embodiment there is more than one port at least one port dedicated for accepting a charge of therapeutic agent into the diffusion device and at least one port dedicated for expelling the contents of the diffusion device.

In another embodiment the one or more ports are modular ports installed sometime after manufacture of the diffusion device and before initial use of the diffusion device. In another embodiment the system includes at least one pre-installed port and at least one port installed after manufacture of the diffusion device and before initial use of the diffusion device. In the embodiment with installable ports the ports comprise a flange and a stem protruding up from the flange. In this embodiment the installable ports are installed to the external device layer using an adhesive provided on the flange and wherein the ports are activated by puncturing the device layer at the base of the stem.

In one embodiment the ports are self-sealing ports. In one embodiment the agent delivery mechanism is an injection needle connected to a charge device loaded with therapeutic agent under pressure. In another embodiment the delivery mechanism is an injection needle connected to a syringe. In another embodiment the delivery mechanism is a tube connected to a continuous agent delivery system.

In one embodiment there is a single port used both for introduction of the therapeutic agent and for evacuation of contents. In one embodiment the contents evacuated are one of a fluid, wound exudates, a gas, or an expired or residual therapeutic agent.

According to another aspect of the invention a method is provided for evacuating the contents of and then introducing a therapeutic agent into a diffusion device the diffusion device characterized as having at least one interior reservoir accessible through a penetrable external device layer and a diffusion layer comprising the steps (a) activating a port installed on the device by puncturing a seal in the port, (b) applying physical pressure on the external device layer expelling the contents of the device through the open port, (c) inserting a delivery mechanism into the port, (d) introducing the therapeutic agent into the device, and (e) sealing off the port.

In one aspect of the method in step (b) the contents comprise air or an inert gas. In one aspect the port is installed during manufacture of the device. In another aspect the port is installed after manufacture and before initial use of the device. In one aspect of the method the steps are all practiced while the device is attached to tissue of a patient being treated. In one aspect in step (d) the therapeutic agent is one of a gas, a gel, a liquid, an emulsion, a drug, a growth factor, an analgesic, an antibiotic, or an antimicrobial. In one aspect of the method in step (b) evacuation of the device contents is performed by an evacuation pump connected to the open port.

DETAILED DESCRIPTION

The inventor provides at least one improved system and methods for charging a diffusion dressing for treating damaged tissue with therapeutic agent and for evacuating the same of air, exudates or expired therapeutic agent before and during application of the device in active tissue treatment therapy. The present invention is described in enabling detail in the various embodiments described below.

Figure 1:
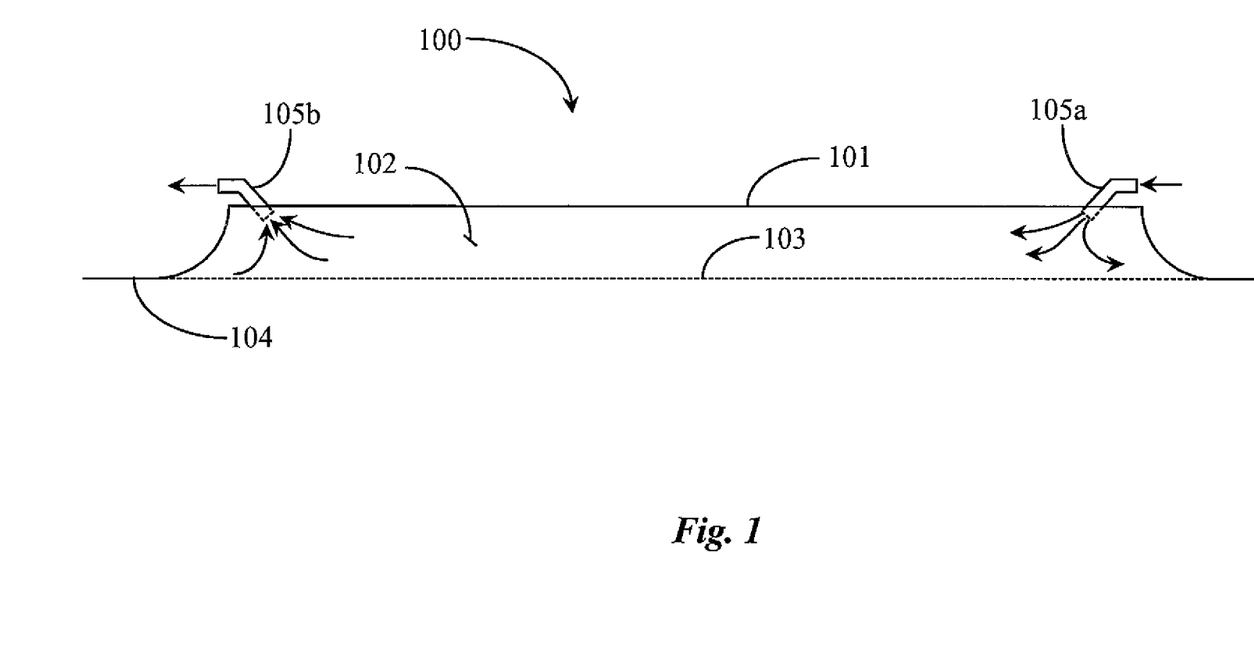
FIG. 1 is an elevation view of a diffusion device with one or more built-in ports for charging and evacuation according to an embodiment of the invention.

FIG. 1 is an elevation view of a diffusion device with one or more built-in ports for charging and evacuating according to an embodiment of the invention. A multi-layered diffusion device 100 is illustrated in this example. Device 100 is adapted diffuse a therapeutic agent from one or more internal reservoirs 102 through a device diffusion layer 103 onto tissue of a wound. Device 100 is sealed onto a patient over a wound site by a peripherally disposed sealing or adhesive layer 104. An occlusive layer 101 of the device enables the device to retain a charge of therapeutic agent. It is noted herein that in some embodiments layer 101 may be permeable.

In one embodiment an additional (removable) impermeable layer may be provided to cover diffusion layer 103 and peripherally disposed adhesive layer 104. Diffusion device 100 has at least one built-in port that can be used for charging one or more reservoirs of device 100 and/or for evacuating air, wound exudates or expired therapeutic agents from one or more reservoirs of the device. In this example a built-in port 105a is provided near one edge of diffusion device 100. Port 105a may be a dedicated input port such as a one-way valve common to certain medical devices like intravenous (IV) solution ports. Port 105s may also be two-way valve that enables evacuation and charging of one or more reservoirs 102 of device 100. In this example port 105a is a one-way valve for charging device 100 and another port 105b is provided for evacuating device 100.

Having two ports, one for charging and one for evacuation may be helpful to avoid cross contamination if a different therapeutic agent is used to replace another during treatment or if wound exudates need to be removed before a next dose or charge of agent. A therapeutic agent may include but is not limited to a gas, a gel, a liquid, an emulsion, a drug, a growth factor, an analgesic, an antibiotic, an antimicrobial, a saline solution, or any other compound. In one embodiment ports 105a and 105b are installed into device 100 during manufacture of the device and are self sealing ports. Port 105a may be an injection port for introducing therapeutic agent into reservoir(s) 102 of device 100 as indicated by the directional arrows. The method of delivery may be by injection needle, by tube delivery, or by other method depending on the type of agent used and duration of delivery, which may vary.

In one embodiment, port 105b is a dedicated evacuation port for evacuating air, therapeutic agent, or exudates from reservoir or reservoirs 102. Port 105b may be a self sealing port. The mechanics of self sealing valves or ports are well known in the art and available in a variety of valve structures. For example, when a delivery needle for example is pushed into a self-sealing valve the valve opens to accept the needle and forms a seal around the needle while it is inserted. After injecting a therapeutic agent the needle may be removed and the valve immediately seals itself upon withdrawal of the needle.

In one embodiment ports 105a and 105b are bi-directional ports that can be manually sealed after use by heat seal or delivery of a sealing substance like a liquid sealant or epoxy that hardens to form an impermeable seal. A syringe needle or other elongate tubular member (not illustrated) may serve to inject therapeutic agent or to evacuate air, therapeutic agent, or exudates from the reservoir or reservoirs of diffusion device 100. Diffusion device 100 may be charged and evacuated while adhered to a patient and does not have to be removed to charge, evacuate, or re-charge the device. Ports 105a and 105b may be manufactured of flexible medical grade polymers and can be installed during manufacture of diffusion device 100.

It is noted herein that diffusion device 100 may include multiple reservoirs instead of a single reservoir. The reservoir walls of a diffusion device having multiple reservoirs may be permeable such as through provision of micro-perforations, for example, enabling a single port to charge multiple reservoirs from one installed location on the diffusion device. In a case where there may be more than one reservoir in a diffusion device where the reservoirs are self-contained having impermeable walls, there may be a port provided for charging and evacuating each reservoir without departing from the spirit and scope of the present invention.

Figure 2A:
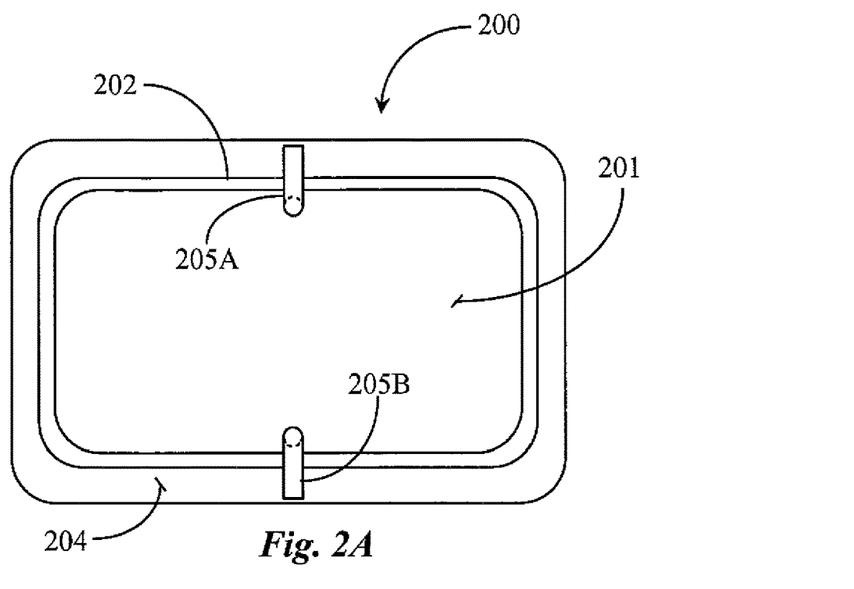
FIG. 2A is an overhead view of a diffusion device with one or more built-in ports for charging and for evacuating the device.
Figure 2B:
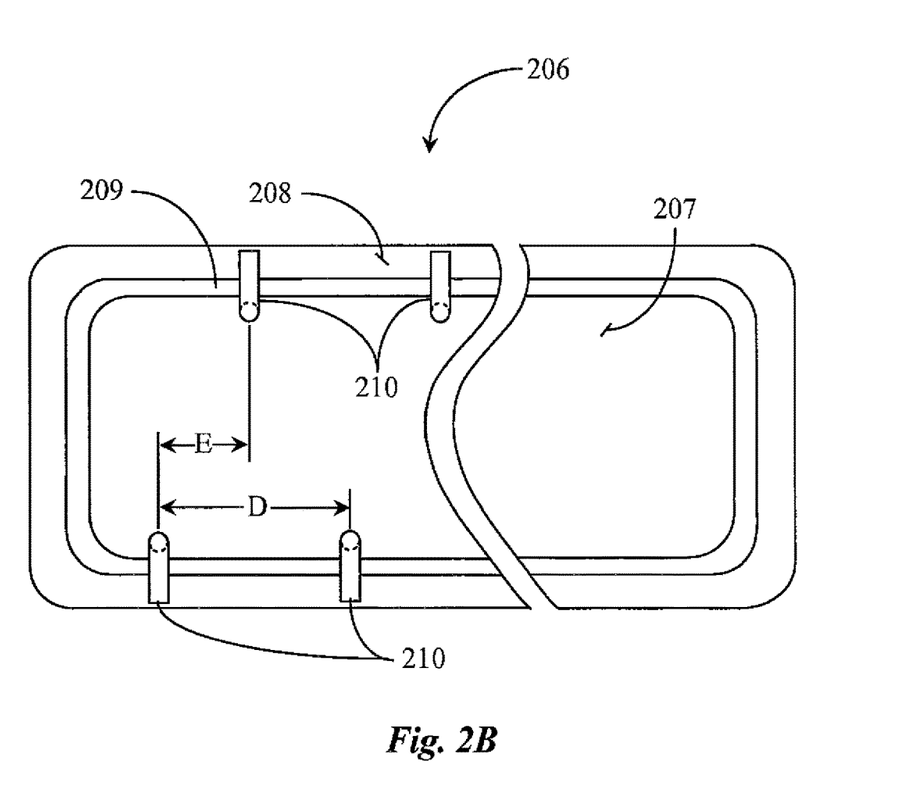
FIG. 2B is an overhead view of a diffusion device with a variable length in one direction having multiple built-in ports for charging and for evacuating the device.

FIG. 2A is an overhead view of a diffusion device 200 with one or more built-in ports for charging and for evacuating the device. FIG. 2B is an overhead view of a diffusion device 206 with a variable length in one direction having multiple built-in ports for charging and for evacuating the device. Referring now to FIG. 2A, device 200 is analogous in construction to device 100 described above. Device 200 includes an occlusive layer 201 and an adhesive layer 204. The side wall of device 200 is illustrated herein as sidewall 202.

Device 200 is rectangular in this example however it may be manufactured in the form of different geometric shapes. In this example there are two ports 205A and 205B built into diffusion device 200. Ports 205A and 205B are installed into device 200 and may be analogous in construction to ports 105A and 105B describe further above. For example, port 205A may be an injection port while port 205B may be an evacuation port. In one embodiment only a single port is provided through which the device may be charged and evacuated. Ports 205A and 205B may be self sealing ports or they may be open ports that can be manually sealed off. A self-sealing port is more convenient in cases where repeated periodic infusions of therapeutic agent are required while the diffusion device is in use on a patient. A port that is manually sealed may also be reopened and resealed a number of times depending on the sealing method.

In this example ports 205A and 205B are disposed opposite one another and symmetrically aligned with one another although this is not required. Referring now to FIG. 2B, a diffusion device 206 is illustrated and is of the same general construction as device 200 of FIG. 2A with an exception that a dimension in one direction (length) is not predictable or defined as is the case with diffusion device 200 described above. Device 206 has an occlusive layer 207, a sidewall 209 and an adhesive layer 208 visible in overhead view of the device. In a case of an elongated device such as device 206, multiple ports 210 are provided in equally spaced intervals (dimension D) along the edges of the device, in this example, in the direction of the variable length dimension of the device.

Ports 210 may be injection ports only or they may be a mix of injection and evacuation ports placed alternately along each edge of device 206. Ports 210 may be self sealing ports or they may be open ports that are manually sealed after charge and after evacuation. Ports 210 may be open ports that are pre-sealed before use requiring a seal to be broken in order to access the interior or reservoir of device 206. Ports 105 and 205 described further above may also be open and pre-sealed ports. Ports 210 may be disposed only along one edge of device 206 and are not required along both edges of the device. Ports 210 are installed in device 206 during manufacture of the device. In this example the array of equally spaced ports installed along one edge of device 206 is offset from the opposing array of ports along the other edge by one half of dimension D illustrated herein as dimension E. In no way is this arrangement of ports required to practice the present invention. Some or all of the ports may be used to charge and evacuate device 200.

Referring now to FIG. 1, FIG. 2A and FIG. 2B pre-installed ports 105, 205, and 210 are illustrated as installed through the top occlusive layer of the device. In one embodiment ports may be pre-installed through the sidewall of the device instead or in addition to installation through the top layer of the device. In all of the embodiments thus far described, the pre-installed ports extend through the top layer of the host diffusion device into the interior of the device in order to intimately communicate with one or more reservoirs provided therein.

Figure 3:
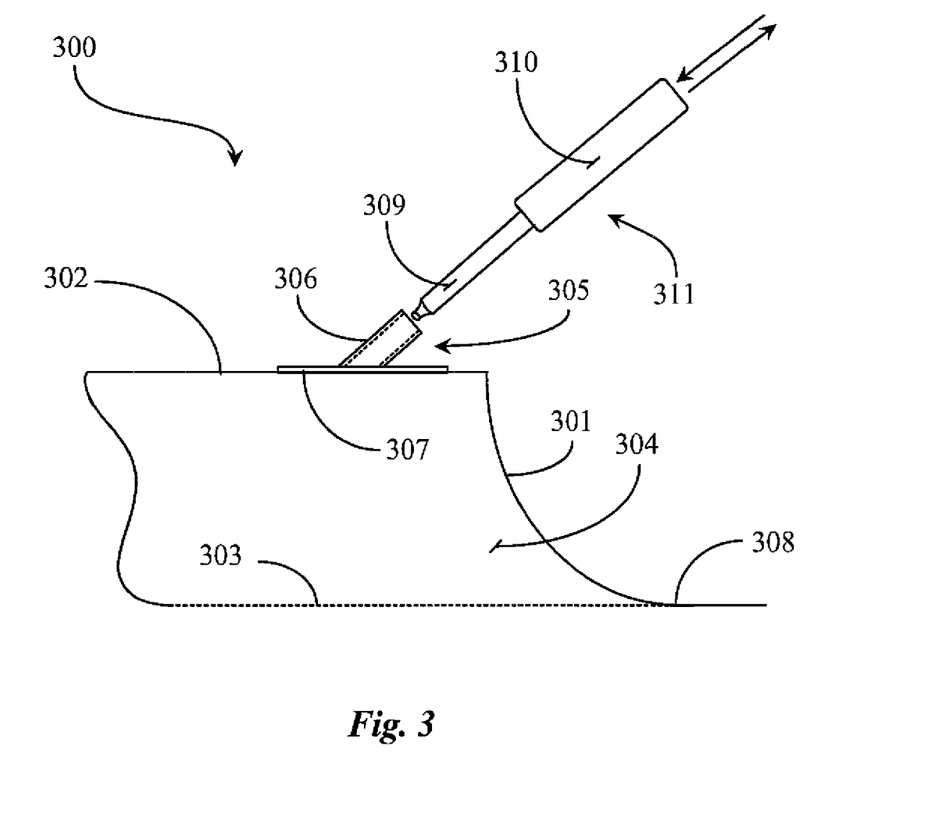
FIG. 3 is an expanded view of an edge portion of a diffusion device illustrating an installable port and injection apparatus according to another embodiment of the invention.

FIG. 3 is an expanded view of an edge portion of a diffusion device 300 illustrating an installable port and charging apparatus according to another embodiment of the invention. Diffusion device 300 is analogous in construction to devices described further above. Device 300 has an occlusive layer 302, a side wall 301, a diffusion layer 303, one or more reservoirs 304, and an adhesive layer 308 all of which may be analogous to counterparts described above with respect to the diffusion devices of FIG. 1 and FIGS. 2A and 2B.

A difference in device 300 from previously introduced devices is that it does not include a pre-installed port for charging or evacuation. Rather, a modular port 305 is provided to be installed at a time that charging and or evacuation of the diffusion device is appropriate. An appropriate time for charging and or evacuating diffusion device 300 may be just prior to application or during application of the device on a patient. Port 305 includes a tubular stem 306 that protrudes upward from an annular flange 307. Flange 307 and stem 306 are contiguously formed in one embodiment such as by a molding process.

Port 305 may be manufactured from a medical grade polymer and may be rigid or somewhat flexible. An industrial grade adhesive layer may be provided on the interfacing surface of flange 307 and may be protected by a removable film. A user may position port 305 over device 300 and may press the device flat onto occlusive layer 302 of device 300 after removing the protective film to expose the adhesive layer. In one embodiment a user might apply an adhesive to the undersurface of flange 307 before pressing the port onto the diffusion device. In this example, stem 306 protrudes upward from flange 307 at a notable angle. In one embodiment the stem may be substantially perpendicular to the flange.

Stem 306 may be open at the intersection of the stem and flange 307. A puncture is required at the base of stem 306 through the center of flange 307 and through occlusive layer 302 in order to activate the port for charging the device or for evacuating the device. In one embodiment device 300 may be outfitted with more than one port such as port 305 wherein one port may be used for evacuation and the other for charging. In one embodiment the ports are color coded to indicate which port should be used for introduction of therapeutic agents and which port should be used to evacuate exudates from the wound tissue.

In this example an injector device 311 is illustrated having a delivery needle 309 affixed to a cartridge 310. Such a device may be pre-charged with a therapeutic gas, for example, kept under pressure and then discharged into diffusion device 300 to effect charging of the device. A switch or lever on the cartridge may be provided to break a seal (not illustrated) between the cartridge and needle and allow the gas to escape the cartridge through delivery needle 309. The tip of needle 309 may be used to puncture surface 302 within the confines of stem 306.

In another embodiment a syringe may be used as a delivery system for delivering a therapeutic agent into diffusion device 300. In one embodiment, therapeutic agent may be delivered through port 305 into one or more reservoirs of diffusion device 300 from a continually connected delivery system. Such a system may have delivery apparatus that connects onto stem 306 of port 311 in a secure manner (without leakage) while the diffusion device is in use on a patient. Such a delivery system may be adapted for regulated delivery of therapeutic agent in continuous manner or in intermittent charges as required. In the case of intermittent charges, several charges may be made to the diffusion device before any evacuation of exudates, for example, would be necessary as the gas agent would escape the device through the diffusion layer and into tissue being treated.

Figure 4A:
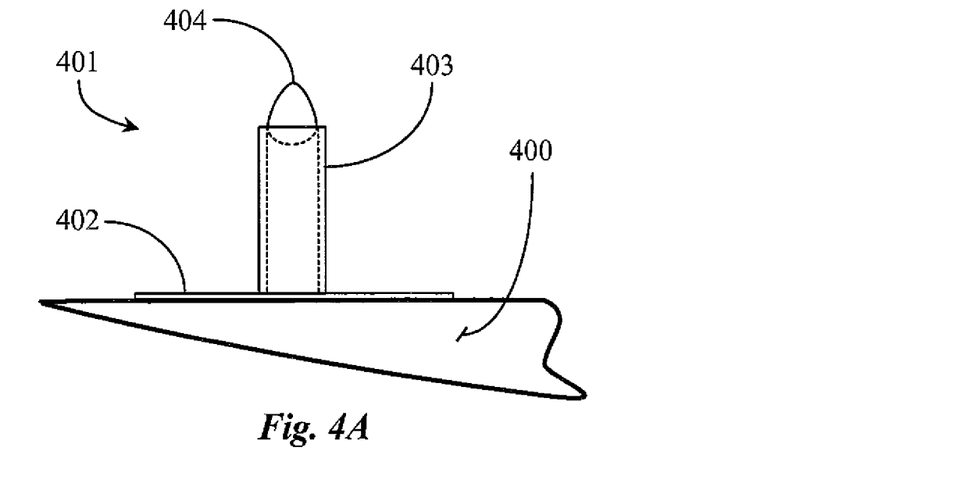
FIG. 4A is an expanded view of a port installed on a diffusion device surface and sealed off according to an embodiment of the present invention.
Figure 4B:
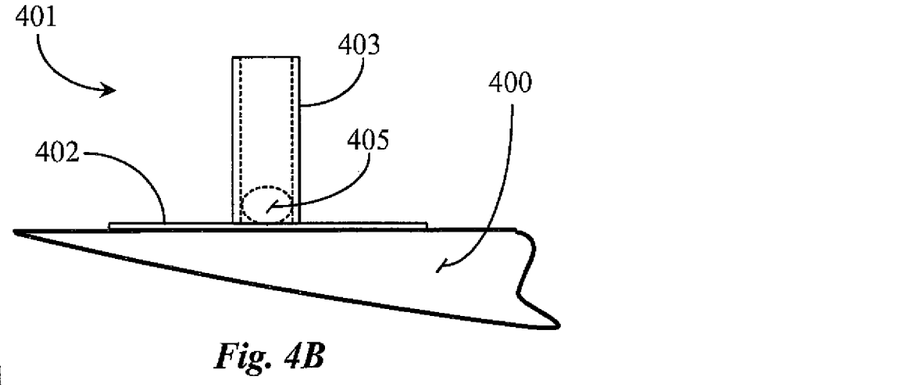
FIG. 4B is an expanded view of the port of FIG. 4A sealed off in another way.
Figure 4C:
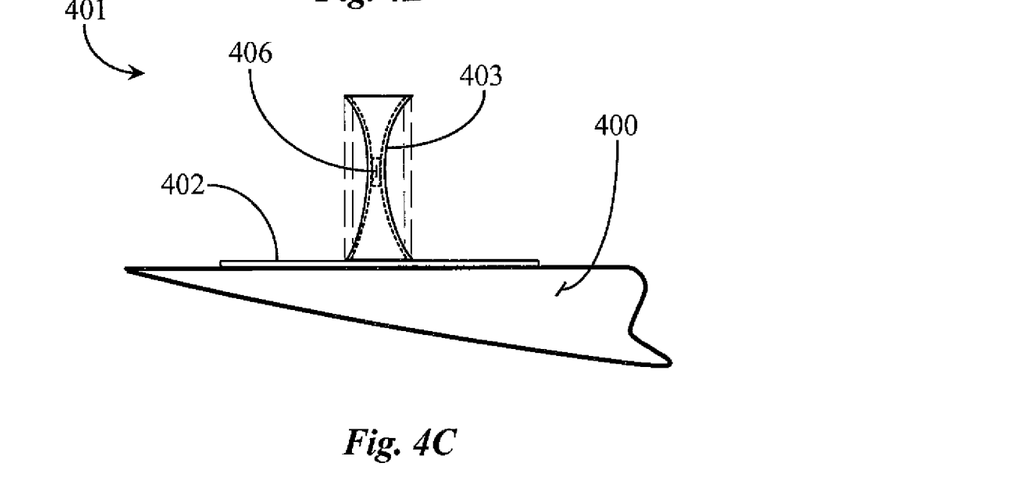
FIG. 4C is an expanded view of the port of FIG. 4A sealed off in yet another way.

FIG. 4A is an expanded view of a port 401 installed on a diffusion device surface and sealed off according to an embodiment of the present invention. FIG. 4B is an expanded view of the port of FIG. 4A sealed off in another way. FIG. 4C is an expanded view of the port of FIG. 4A sealed off in yet another way. Referring now to FIG. 4A port 401 is a modular port adhered to the surface of a diffusion device represented herein as a broken surface 400.

In another embodiment port 401 may be a pre-installed port like ports 105(a,b), 205(a,b), and 210 described further above. In this case port 401 has an adhesive flange 402 and a stem 403 that protrudes up from flange 402, in this case, substantially perpendicular to the flange. It is assumed in this example that the surface of device 400 has already been punctured at the base of stem 403 within the confines of flange 402. Port 401 is sealed off (seal 404) in this case at the top of stem 403. The mechanics of seal 401 may be that of a liquid sealing substance that cures and hardens to provide a leak-proof seal. Breaking seal 404 for the purpose of a subsequent charge, for example, may be accomplished by puncturing seal 404 or by trimming it off of stem 403 just below the bottom surface of the seal.

Referring now to FIG. 4B, port 401 is sealed off at the base of stem 403 rather than at the top of the stem. A seal 405 is forged near or at the bottom of the stem effectively closing the puncture previously made to open or activate the port for initial use. Seal 405 may be breached by re-puncturing to reopen the port. Resealing may also occur in the same fashion described when required after charging. Referring now to FIG. 4C, stem 403 is caused to collapse upon itself to form a seal 406. In one embodiment this may be accomplished using heat and a crimping tool. Referring now to FIGS. 4A-C, port 401 may be a dedicated evacuation port.

Figure 5:
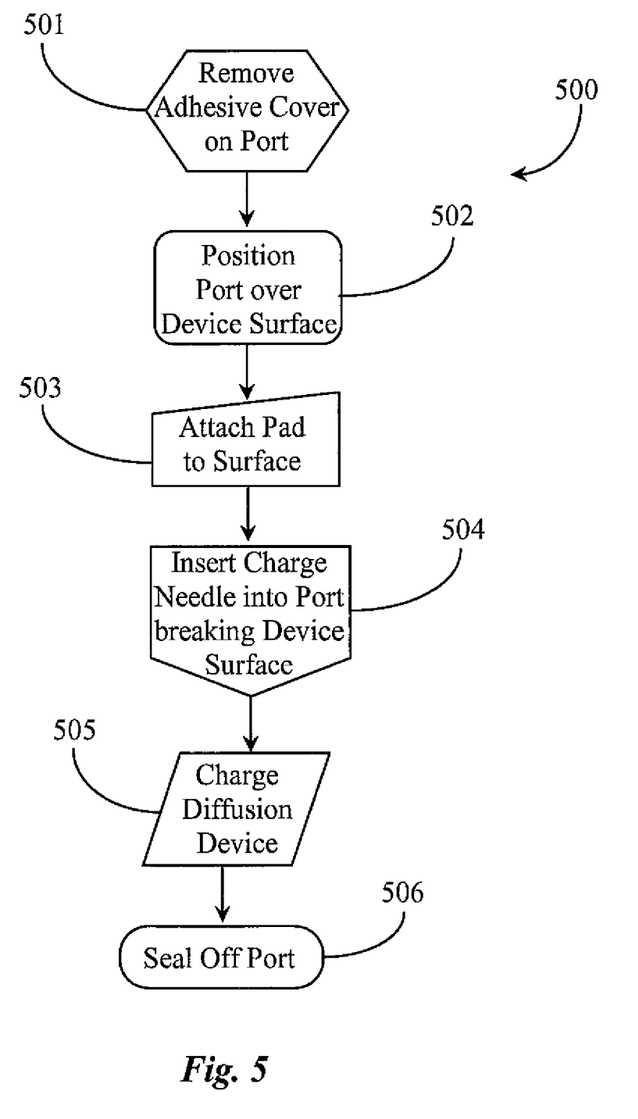
FIG. 5 is a process flow chart illustrating steps for installing a modular port to a diffusion device and charging the device.

FIG. 5 is a process flow chart illustrating steps for installing a modular port to a diffusion device and charging the device. At step 501 the user installing the port on the diffusion device first removes an adhesive over or film from the flange of the device. The adhesive may be a type that cures to a permanent and durable hermetic seal. At step 502 with the adhesive cover removed the user position the port over the device surface at a desired location.

At step 503 the user attaches the flange or port pad to the device surface by pressing the flange against the surface material. The adhesive may be fast curing adhesive. After the adhesive is cured and the port is secured to the diffusion device, the port may be activated for use. At step 504, the user may insert a charge needle or other puncture device into the port stem to break or puncture the surface of the diffusion device thereby activating the port to accept a charge or for the purpose of reservoir evacuation. In the case of charging, the user may charge the diffusion device with a therapeutic agent. At step 506 the user may seal off the port using any one of the methods previously described above.

In one embodiment the port is not sealed off at step 506 because the charging apparatus is continually connected to the diffusion device while it is being used. In this case the device is in use on a patient and is active in wound therapy.

Figure 6:
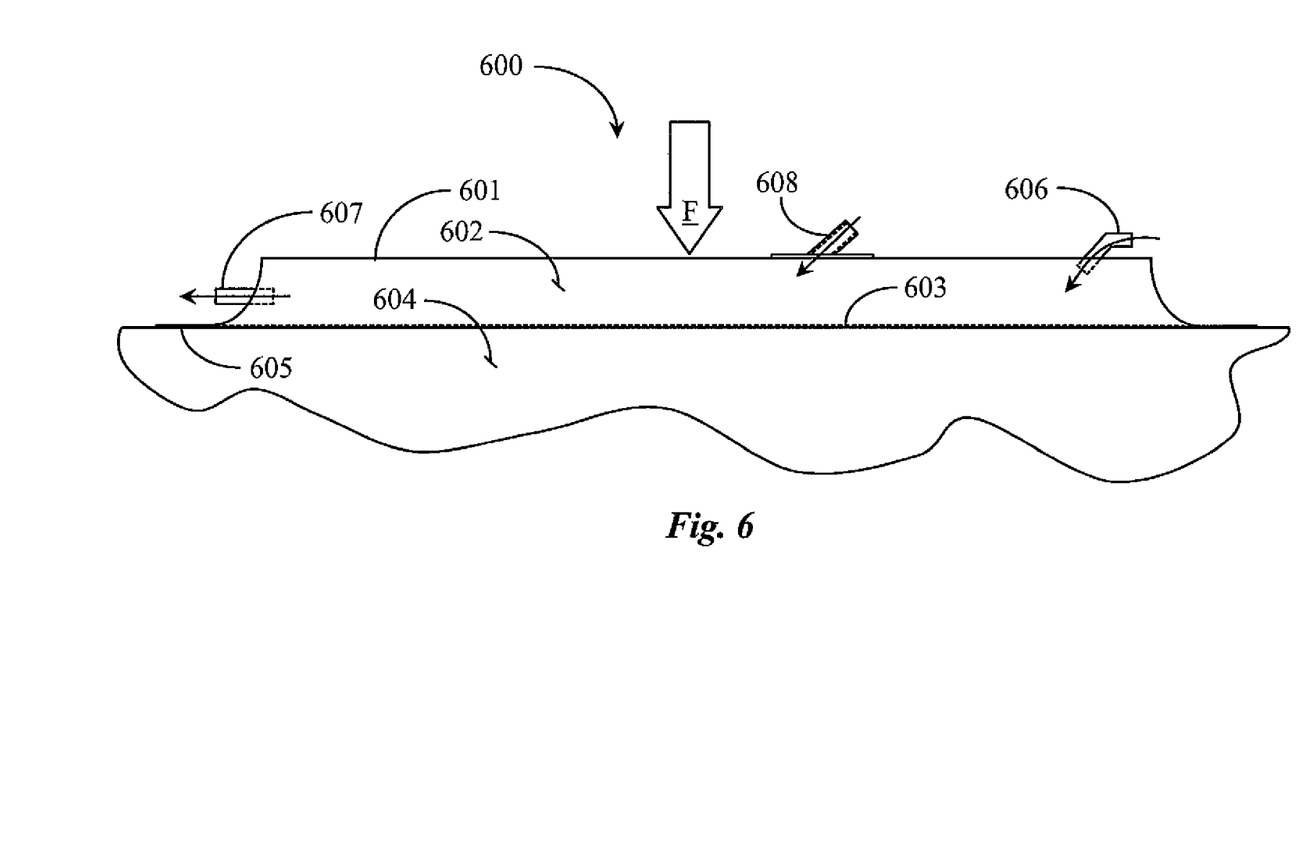
FIG. 6 is an elevation view of a diffusion device void of therapeutic agent having one or more ports for charging and evacuating the device while it is applied to a wound.

FIG. 6 is an elevation view of a diffusion device 600 void of therapeutic agent having one or more ports for charging and evacuating the device while it is applied to a wound. Diffusion device 600 is analogous in construction to other diffusion devices described above and includes an occlusive layer 601, a diffusion layer 603, an adhesive layer 605, and one or more reservoirs 602. In this example, device 600 is adhered to a tissue illustrated herein as tissue 604 by virtue of adhesive layer 605 extending peripherally around the device.

In this case device 600 is void of therapeutic agent but may contain a volume of air or another inert gas within reservoir 602. A pre-sealed vacuum port 607 might be provided on device 600 in one embodiment. Port 607 may be activated by breaking or otherwise compromising the seal and force illustrated herein by an arrow labeled F might be applied by a user to evacuate any air or inert gas that might be inside reservoir 602 through port 607 as is indicated by a directional arrow. Port 607 may then be resealed and the device may be charged while in place on the patient.

Device charging may occur through a pre-installed port like port 606 or by installing and activating a modular port like port 608. Port 608 is activated by puncturing the surface 601 of device 600 after the port is installed. Port 606 may be activated by breaking or otherwise compromising a seal. In one embodiment device 600 is not pre-charged with any inert gas or other substance before use and exiting ports are not pre-sealed. In one embodiment device 600 may be pre-evacuated before a first charge by pulling a vacuum through port 607 instead of applying manual pressure to the top of the device.

Figure 7:
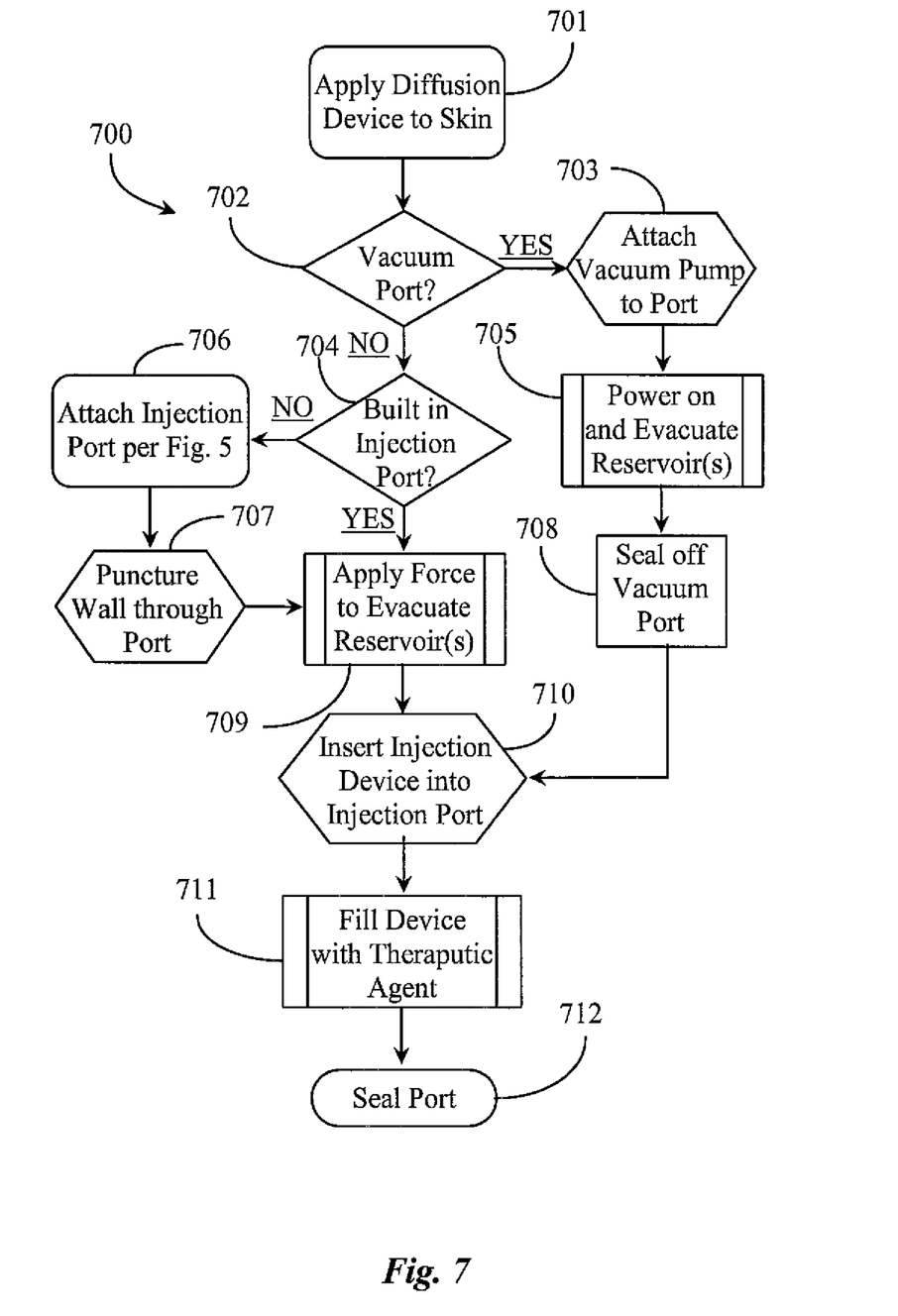
FIG. 7 is a flow chart illustrating steps for preparing a diffusion device for first use according to variant aspects of device architecture.

FIG. 7 is a flow chart illustrating steps 700 for preparing a diffusion device for first use according to variant aspects of device architecture. It is assumed in this example that the diffusion device is void of therapeutic agent and is to be evacuated before initial charge. At step 701 a user or a practitioner may apply or attach the diffusion device to the skin of a patient. At step 702 it is determined if there is a vacuum port on the device. If at step 702 if there is a vacuum port on the device at step 703 a vacuum pump is attached to the port. In one embodiment the vacuum port may be pre-sealed and an inert gas or air may be held within one or more reservoirs of the diffusion device. In this case the seal may be broken before the vacuum pump is attached at step 703.

At step 705 the pump is powered on and the diffusion device is evacuated. At step 708 the vacuum port is sealed off to prevent any leakage of therapeutic agent when charged. At step 710 an injector may be inserted into an injection port provided on the device. An injection port may be assumed to be provided if an evacuation port is provided. At step 711 the diffusion device is filled with a therapeutic agent. At step 712 the injection port may be sealed off to prevent leakage of therapeutic agent back out of the injection port. In one embodiment the injection port is a one way valve and is self sealing. In this case step 712 is not required.

Referring now back to step 702 in the process, if there is no vacuum port provided on the device it is determined at step 704 if there is a pre-installed (built-in) injection port. If there is an injection or charge port installed on the diffusion device then it is assumed that the device may be evacuated and charged through the same port. In this regard the port would be bi-directional. At step 709 the user may apply force to the top of the diffusion device in order to evacuate any air or inert gas from inside the reservoir(s) of the device.

The process moves to step 710 where an injection device or other therapeutic agent delivery mechanism is inserted into the injection port. At step 711 the diffusion device is filled with a therapeutic agent and at step 712 the injection port is sealed. Back at step 704 if it is determined that there is no pre-installed injection port then the device has no ports. At step 706 the user or practitioner may install a modular injection port to the diffusion device per the process described previously in the detailed description of FIG. 5.

At step 707 the practitioner punctures the wall of the diffusion device through the port stem of the installed port, perhaps with the needle of the injection device. The process then moves to step 709 evacuating the device by applying pressure to the top surface of the device. At step 710 the charging needle or apparatus is inserted into the port and at step 711 the diffusion device is charged. After the device is charged, the port may be sealed at step 712. It will be apparent to one with skill in the art that process steps 700 may include more or fewer steps than illustrated here and that other process branches may occur depending at least in part on device architecture including provision of ports and the therapeutic agent used. In one embodiment the device is pre-charged with air or an inert gas. In another embodiment the device is not pre-charged but may contain air that may need to be evacuated.

In one embodiment a system of charging and evacuation is observed wherein the diffusion device is evacuated of exudates and sterilized, neutralized, or otherwise cleansed before a next charge of therapeutic agent is introduced into the device. Therefore a charge may be designed only to neutralize or cleanse the inside of the device followed by an evacuation and a re-charge of active therapeutic agent. In this case alternate therapeutic agents may be used to treat tissue in a manner that maximizes recovery and keeps the tissue clean from agent residue, infectious matter, or other containments. In some cases where different agents may unfavorably react if mixed neutralization or cleansing charge followed by an evacuation may enable safer use of the different compounds.

Figure 8:
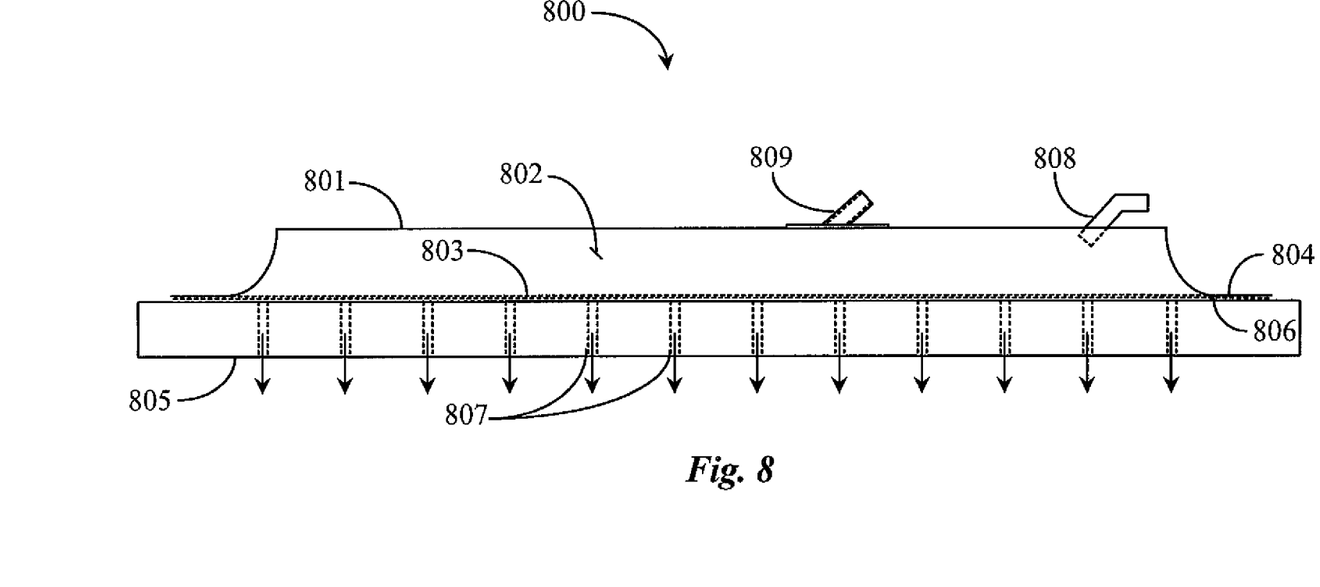
FIG. 8 is an elevation view of a diffusion device having at least one injection port positioned on an evacuation plate according to an embodiment of the invention.

FIG. 8 is an elevation view of a diffusion device 800 having at least one injection port positioned on an evacuation plate according to an embodiment of the invention. Diffusion device 800 is constructed similarly to other diffusion devices described previously. Device 800 has an occlusive layer 801, one or more reservoirs 802, a diffusion layer 803, and an adhesive layer 804. In this example, diffusion device 800 may include one or more injection ports such as pre-installed port 808 or modular port 809. An evacuation port may or may not be provided.

In this embodiment diffusion device 800 is void of therapeutic agent but is evacuated to remove air or inert gas through the diffusion layer 803. A vacuum surface plate 805 is provided in the form of a sold and flat plate containing a plurality of vacuum passages 807 through which air or inert gas in one or more device reservoirs may be evacuated. Plate 805 may be part of a vacuum pump system where the plate is part of a hand held vacuum hose apparatus.

A special permeable removable layer 806 is provided to cover diffusion layer 803 and, in this case the area of adhesive layer 804. This removable layer is permeable to enable evacuation of the contents of diffusion device 800. Plate 805 may be manufactured of a durable polymer, aluminum, or some other metal. Plate 805 may be much larger in area than the diffusion device in order to accommodate diffusion devices of the different area footprints. Layer 806 protects the diffusion layer from direct contact with the surface of the vacuum plate avoiding possible contamination before tissue application.

In one embodiment of the present invention a diffusion device such as device 800 may be charged with therapeutic agent at the time of use but before the device is actually applied to a tissue area. In this case the vacuum may be shut off completing evacuation and subsequently a charging device or system may be connected to port 808 or to port 809 to fill the device with therapeutic agent. After filling device 800 with therapeutic agent, the release layer 806 may be removed and the device may be adhered to a targeted tissue area.

It will be apparent to one with skill in the art that the system for charging and evacuating system and methods of the invention may be provided using some or all of the mentioned features and components without departing from the spirit and scope of the present invention. It will also be apparent to the skilled artisan that the embodiments described above are exemplary of inventions that may have far greater scope than any of the singular descriptions. There may be many alterations made in the descriptions without departing from the spirit and scope of the present invention.

What is claimed is:

1. A diffusion device comprising:
   an impermeable external device layer;
   a diffusion layer sealed to the impermeable external device layer around a periphery of the impermeable device layer, forming a reservoir volume between the diffusion layer and the external device layer, the reservoir volume charged with a therapeutic agent to a pressure above ambient pressure;
   an adhesive region extending outwardly around a periphery of the impermeable device layer, enabling the diffusion device to be adhered around a periphery of a wound;
   a removable, impermeable protective layer covering the diffusion layer and the adhesive region;
   a one-way charging port installed through the external device layer, the port when closed enabling the reservoir volume between the impermeable device layer and the diffusion layer to maintain a pressure above ambient pressure in the reservoir volume; and a self-closing evacuation port dedicated to withdrawing material from the reservoir volume;

wherein, with the removable, impermeable protective layer removed, the diffusion device is sealed over a wound site, via the adhesive, and the therapeutic agent diffuses through the diffusion layer to the wound, and wherein, material may be removed via the dedicated evacuation port, and therapeutic agent may be added through the one-way charging port after application of the diffusion device over the wound site.

2. The system of claim 1 wherein the therapeutic agent is one of a gas, a gel, a liquid, an emulsion, a drug, a growth factor, an analgesic, an antibiotic, or an antimicrobial.

3. The system of claim 1 wherein ports are built-in with the diffusion device.

4. The system of claim 1 wherein the ports are modular ports enabled to be installed just prior to initial use of the diffusion device.

5. The system of claim 1 comprising at least one built-in port and at least one modular port.

6. The system of claim 4 wherein the ports comprise a flange and a rigid stem protruding up from the flange.

7. The system of claim 6 wherein the ports are installed to the external device layer using an adhesive provided on the flange and wherein the ports are activated by puncturing the device layer at the base of the stem.

* * * * *